United States Patent [19]
Green

[11] Patent Number: 5,702,669
[45] Date of Patent: Dec. 30, 1997

[54] APPARATUS METHOD FOR STERILIZATION USING ETHYLENE OXIDE

[76] Inventor: Edward Francis Green, 330 Flat Roof Mill Rd., East Swanzey, N.H. 03446

[21] Appl. No.: 576,284

[22] Filed: Dec. 21, 1995

[51] Int. Cl.$^6$ ............................................. A61L 9/00
[52] U.S. Cl. ........................ 422/30; 422/33; 422/34; 422/287; 422/288; 422/295; 422/307
[58] Field of Search ........................... 422/30, 33, 34, 422/287, 288, 290, 295, 307

[56] References Cited

U.S. PATENT DOCUMENTS

| | | | |
|---|---|---|---|
| 4,201,745 | 5/1980 | Zickgraf | 422/199 |
| 4,284,600 | 8/1981 | Gillis | 422/26 |
| 4,894,207 | 1/1990 | Archer et al. | 422/292 |
| 4,971,761 | 11/1990 | Johnson | 422/34 |
| 4,974,663 | 12/1990 | Nakaji | 165/1 |
| 5,277,875 | 1/1994 | Albright et al. | 422/109 |
| 5,399,314 | 3/1995 | Samuel et al. | 422/34 |

*Primary Examiner*—Nina Bhat
*Attorney, Agent, or Firm*—George W. Dishong

[57] ABSTRACT

A method and gas sterilizing unit for gas sterilization of a product. The method and gas sterilizing unit obviates the need of a separate preconditioning area or cell, the need to transfer items being sterilized to a separate sterilizing chamber and the need to further transfer the sterilized items to a separate degassing cell or area or room. The gas sterilizing unit comprises a corrugated wall structure which defines a chamber therein, at least one door opening into the chamber, a device for heating and cooling of the chamber, a source of pressure and vacuum, a mechanism for the recovery of the gas sterilant from within the chamber, a manual control panel or programmed logic controller or a programmable computer or PC for controlling each of temperature, pressure, relativity humidity, and for controlling the flushing of the chamber with nitrogen, the injecting into the chamber of a measured amount of a gas sterilant such as ethylene oxide, the recovery and treatment of the gas sterilant and for control of the timing of each of the steps of the process. The gas sterilizing unit supports the method for gas sterilization in that the method or process can be completed in one and the same sterilizing unit resulting in an increase in efficiency and lower energy consumption. The sterilizing unit and the sterilizing press will permit a dynamic preconditioning cycle where heat and humidity can be introduced to the product under a vacuum and pulsed up and down in pressure. The sterilizing unit and the sterilizing process will also permit the degassing to take place under dynamic conditions which enhances the effectiveness of the process and reduces the time needed to achieve safe levels of ethylene oxide. Worker exposure to product which is outgassing while moving the product from a sterilizing chamber to a degassing room is eliminated.

15 Claims, 3 Drawing Sheets

APPARATUS METHOD FOR STERILIZATION USING ETHYLENE OXIDE

FIELD OF THE INVENTION

The present invention relates generally to a gas sterilizing unit and method of sterilizing a product. More particularly, the invention relates to a gas sterilizing unit where the preconditioning, sterilizing and degassing cycles all occur within a chamber formed by a single corrugated or lightweight structure.

BACKGROUND OF THE INVENTION

Gas sterilizer units utilize gaseous chemicals for sterilizing products such as plastic, rubber, or the like, which cannot withstand heat sterilization. Also, the sterilizing agents or sterilant are commonly used in the fumigation of spices and antiques, and for sterilizing medical devices. Sterilization is complete when a sterilant kills or inactivates the contaminating microorganism. The most common sterilant or sterilizing agent is ethylene oxide hereinafter Traditionally, industry had used a combination of EO and carbon dioxide or Freon 12 to reduce the volatile nature of EO. The common mixture was 12% EO and 88% of Freon 12. Sterilization utilizing the combination of EO and Freon 12 required pressures up to 30 psia in order to achieve concentrations of EO in the range of 500–800 milligrams/liter, to ensure a lethal exposure.

Prior to sterilization, the product is placed in an area for preconditioning. This preconditioning step increases the temperature and humidity in the product to make sterilization more effective.

Present regulations do not mandate preconditioning but accepted practice and procedure call for humidity conditions during sterilization which can only be obtained as a consequence of such preconditioning which is traditionally done by the use of a separate preconditioning area. Regulations are pending which will dictate a validated procedure for preconditioning. Proposed AMMI standards will require validation of the process. Reference is made to ANSI/AMMI/15011135 1994. The preconditioning process is the exposure of a non-sterile product to humidity and heat. The controlled preconditioning of the product helps ensure the maximum effectiveness of the EO. Thereafter, the product is transferred to a sterilizing chamber, where it is exposed to the sterilant (EO). In the process of transferring the product from the separate preconditioning area to the sterilization chamber there is a substantial loss of heat and humidity from the product, which is adverse to the efficiency of the process.

Moreover, the preconditioning process typically occurs in atmospheric pressure where the static penetration of heat and humidity into the product occurs. The static penetration and preconditioning cycle typically requires 12 hours.

The traditional sterilization cycle required a vacuum in the range of 25 inches of mercury (in. Hg) or 2.4 pounds per square inch absolute (psia) and maximum pressures of 30 psia. These operating conditions require that the sterilizing unit have a structure that withstands the vacuum and pressure levels required to sterilize products. The presently used structure is typically manufactured from heavy gauge stainless steel or stainless clad steel, which has a large thermal inertial mass. The large thermal mass dictates that these chambers must be kept at operating temperatures during periods of non use to ensure that they are up to temperature when needed. A chamber of lightweight construction would have to be heated only when in use, resulting in major energy savings.

Subsequent to the sterilization cycle the sterile product was transferred to a separate cell or room to initiate and complete a degassing cycle. The degassing cycle function is to remove residual sterilant (EO) from the product by introducing heated air into the separate degassing cell or area which may be an entire room. The gas/air mixture ambient to the cell or room is then exhausted to the atmosphere at a controlled rate, typically at a rate of 10% of the air handler output for 20 hours.

Modern technology has permitted the use of 100% EO during the sterilization process, while maintaining the practice of preconditioning and degassing the products in separate locations. 100% EO has been used for many years but the use of a nitrogen flush cycle is about 10 years old. Previously the industry accepted the risk that the chamber could have enough oxygen present to contain an explosive mixture and operated their process accordingly. The modern sterilization process requires a series of vacuum cycles to be completed, each vacuum cycle to be following by a nitrogen purge of the chamber. Thereafter, 100% EO is injected into the chamber. The sterilization process typically requires eight hours to complete. The amount of EO is controlled so that the pressure within the chamber is less than atmospheric, such that the sterilizing unit functions under vacuum and not as a pressure vessel.

What is needed is a process for gas sterilization which does not require the use of a separate preconditioning area or cell, the transfer of items being sterilized to a separate sterilizing chamber and the further transfer of the sterilized items to a separate degassing cell or area or room and further, there is need for a sterilizing unit that can support a process for gas sterilization that can be completed in the one and the same sterilizing unit resulting in an increase in efficiency and lower energy consumption. Also, what is needed is a sterilizing process and unit which will permit a dynamic preconditioning cycle where heat and humidity can be introduced to the product under a vacuum and pulsed up and down in pressure. The presently used process utilizes a static preconditioning cycle where heat and humidity are introduced under atmospheric pressure. Also, what is needed is a sterilizing process and unit which will also permit the degassing to take place under dynamic conditions which enhances the effectiveness of the process and reduces the time needed to achieve safe levels of EO. Furthermore, it is extremely important that workers' exposure to product which is outgassing while moving the product from a sterilizing chamber to a degassing room be eliminated. Such exposure is most easily eliminated by having a process and unit which does not require that the product be moved from a sterilizing chamber to a degassing room. The physical movement of the product at this time has the greatest risk of worker exposure in the entire sterilizing process. These and other needs are satisfied by the present invention such as for example it is important to note that the wall structure which defines the chamber design, because the chambers are constructed by a method which allows each unit to be very inexpensive when compared to what is presently used, will allow the use of multiple gas sterilizer units to be used. Each unit will be used for the complete gas sterilization process.

SUMMARY OF THE INVENTION

The invention in its simplest form is a lightweight structure defining an interior portion/chamber therein having structural features which will permit; (1) a vacuum or a pressure within the chamber, (2) the heating of the chamber, (3) the introduction into and the containment within the chamber of a controlled heat and humidity of the gases therewithin, and (4) the introduction into and the containment within the chamber of a controlled amount of a selected gaseous product for use typically as a sterilant.

The preferred embodiment is a gas sterilizing unit that utilizes a sterilant having a chamber or interior portion defined by a corrugated wall structure, such as an aluminum culvert, of lightweight construction, or other appropriate lightweight wall structure with at least one door, and an interior portion or chamber. It is to be noted that, as a very important concept, the design of the wall structure and the sterilizer unit itself will allow the use of multiple chambers to be used for the complete process because they are constructed by a method which allows each unit to be very inexpensive when compared to what is presently used. Also included are: (1) means for controlling temperature of the interior portion i.e., the chamber; (2) means for regulating relative humidity of the interior portion/chamber; (3) means for inserting a controlled concentration of at least one gaseous chemical into the interior portion/chamber and whereby the at least one gaseous chemical such as ethylene oxide (EO) concentrations in the chamber are not measured directly, but are determined by measuring the weight of the gas going in and/or by measuring the increase in pressure in the chamber caused by the partial pressure of the gas, such as EO, used; (4) means for creating a controllable vacuum within the chamber thereby to control the pressure of the gaseous chemical and the removal of the gaseous chemical from the interior portion/chamber and (5) means for timing individual times required for preconditioning, sterilization and degassing the product within the interior portion/chamber of the sterilizing unit. The sterilizing unit takes a non-sterile product and sterilizes the product without transferring the product to multiple locations.

One object of the invention is to provide a gas sterilizing unit that utilizes a method where a product has the preconditioning, sterilizing, and degassing cycles completed in one location, that being within the chamber of such sterilizing unit.

A further object of the invention is to increase the efficiency and decrease the time required to complete the overall process and also provide a substantial reduction in worker exposure to EO.

An additional further object of the invention is to provide a dynamic preconditioning cycle where heat and humidity are introduced to the product under a vacuum.

Another object of the invention is to complete the degassing cycle under a vacuum.

An additional object of the invention is to reduce the possible exposure of EO to the environment and workers, by not transferring the product from a sterilization chamber to a separate degassing location.

Yet another additional object of the invention is to provide a sterilizing unit that may be heated rapidly which saves energy by preventing the necessity of maintaining the unit at operational temperatures.

These and other advantages and features, which characterize the invention, are set forth in the claims annexed hereto and forming a further part hereof. However, for a better understanding of the invention, and the advantages and objectives obtained by its use, reference should be made to the drawing figures, which are a part hereof, wherein like numerals refer to like parts throughout and to the accompanying descriptive matter, in which there is described a preferred embodiment of the invention, and in which:

DETAILED DESCRIPTION OF THE INVENTION

Figure 1:
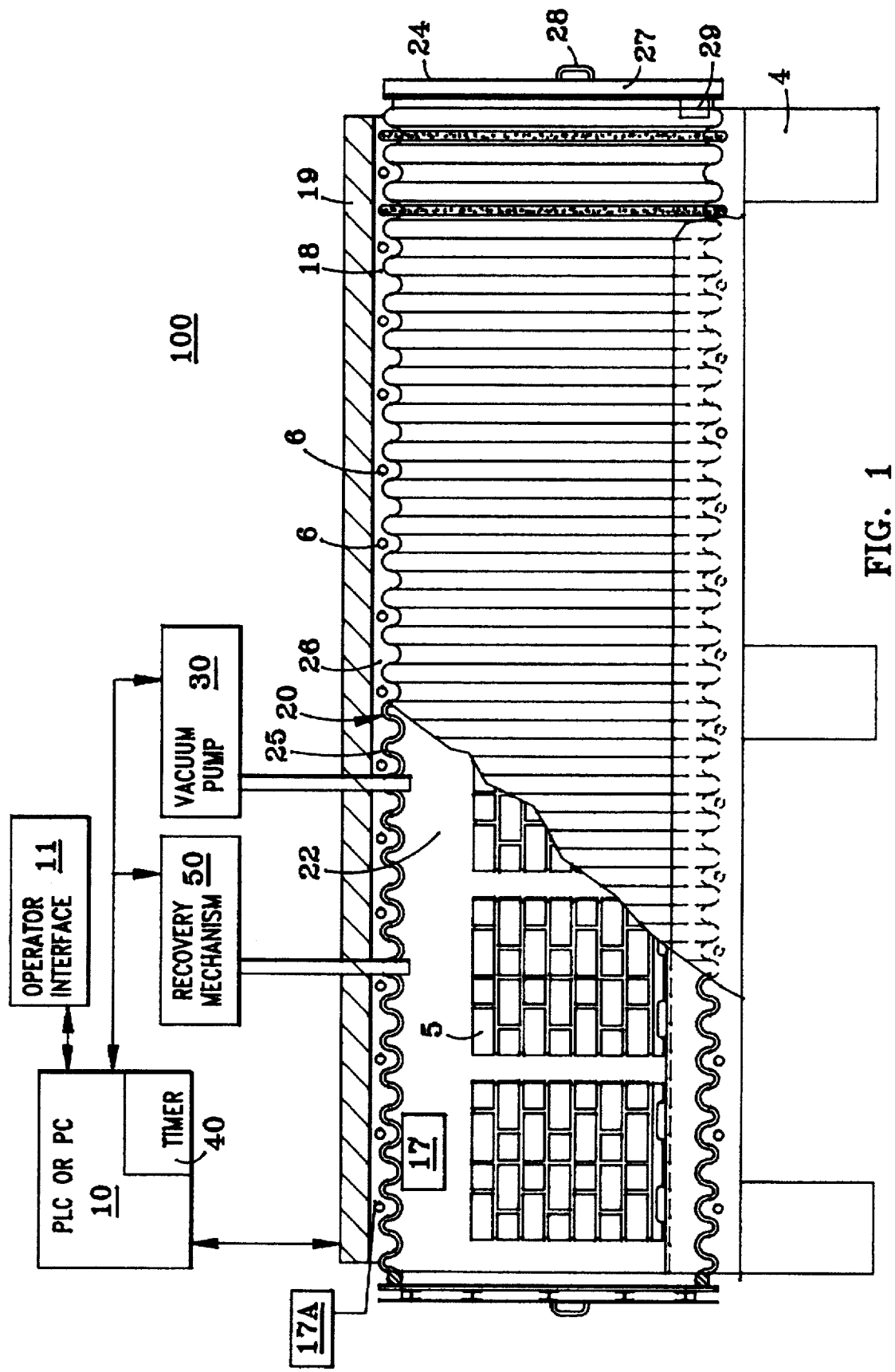
FIG. 1 is a side view of the chamber defined by the corrugated walls of the sterilizing unit, with a cut-away view.

Referring to the drawings, wherein like numerals represent like parts throughout the several views, there is generally disclosed at 100 a sterilizing unit consistent with the principles of the present invention, depicted in FIG. 1.

Although the example of sterilizing a medical product will be discussed herein, those skilled in the art will appreciate that such application is only one of many products in which the principles of the present invention might be utilized. Accordingly, the sterilization of a medical device herein should not be construed in a limiting manner.

Those skilled in the art will appreciate that the single sterilizing unit 100 is illustrated in the drawings. It should be understood that other quantities of sterilizing units 100 may be controlled by a single programmable logic controller or personal computer (herein after PLC/PC 10). It is also understood that the entire process or method for gas sterilization of a product, which product remains within the chamber of the sterilizing unit throughout the entire sterilizing process, may be fully controlled by manual operation of switches and controls. It is not necessary that the process be automated by a PLC or a PC. The level of sophistication of the control of the gas sterilizer unit and of the size of the unit will depend only upon the application for such a unit.

In order to better present and describe the preferred embodiment of the present invention, the detailed description of the process will be deferred pending a discussion of the preferred embodiment of a sterilizing unit.

Referring to FIG. 1, the sterilizing unit 100 having a PLC/PC 10, corrugated wall 20, vacuum pump 30 and a timer 40. Time function could be part of PLC/PC 10. The sterilizing unit 100 may be supported by multiple brackets 4. PLC/PC 10 is configured to control temperature, humidity, concentrations of gaseous chemicals and heating of interior portion/chamber 22 of corrugated wall structure 20 to mention a few of the control functions possible. The PLC/PC 10 also has an operator interact 11 such that programming and monitoring functions are permissible, the operator interface 11 is not required once the programming has been completed. The PLC/PC 10 may be configured to operate multiple sterilizing units 100. The programming of the PLC/PC 10 will be discussed later. A PLC/PC 10 that performs the required functions of the sterilizing unit 100 is well known to one skilled in the art.

Timer 40 is preferably a counter within the PLC/PC 10 that permits individual control of time required for preconditioning, sterilization and degassing product 5. A timer 40 that is integral with a PLC/PC 10 is also well known to one with ordinary skill in the art.

A corrugated wall structure 20 having an internal portion, i.e., chamber 22 and at least one door 24 is provided. Corrugated wall structure 20 has alternating ridges 25 and grooves 26 that are a preferred design in a sterilizer application where a vacuum is utilized. Ridges 25 and grooves 26 also provide additional surface area for heat transfer. The preferable dimensions of corrugated wall structure 20 would vary depending on the size of the product to be sterilized and the total volume needed. The first production model will be 8 feet in diameter and 32 feet long. All diameters and lengths can be custom made including ovaloid and pear shapes. It would be constructed of 8 gauge aluminum or stainless steel. The material chosen is to minimize the inertial mass of the chamber to require less time to heat up to a desired temperature of approximately 125° F. depending on the product. Alternative dimensions and materials of construction are considered to be consistent with the principles of the present invention.

Interior portion or chamber 22 is sized to hold product 5 during the entire process. Medical devices are usually the product 5 which is being gas strerilized. Chamber 22 is configured to permit the entry of instrumentation (not shown) used in the control of the process. Instrumentation that may be used are temperature and pressure sensing devices, such as thermocouples and pressure devices. Components such as thermocouple RTD's and pressure transducers are all readily available and will be selected to be compatible with the designated controller. As stated above, final EO concentrations are not measured directly but are calculated from weight of gas used & pressure changes inside of the chamber.

The instrumentation is approved for hazardous areas such as (Class I, Division 1 or 2, Group B, NEC'93), and is interfaced with the PLC/PC 10 that monitors and controls sterilizing unit 100. The required instrumentation is well known to one skilled in the art.

Figure 2:
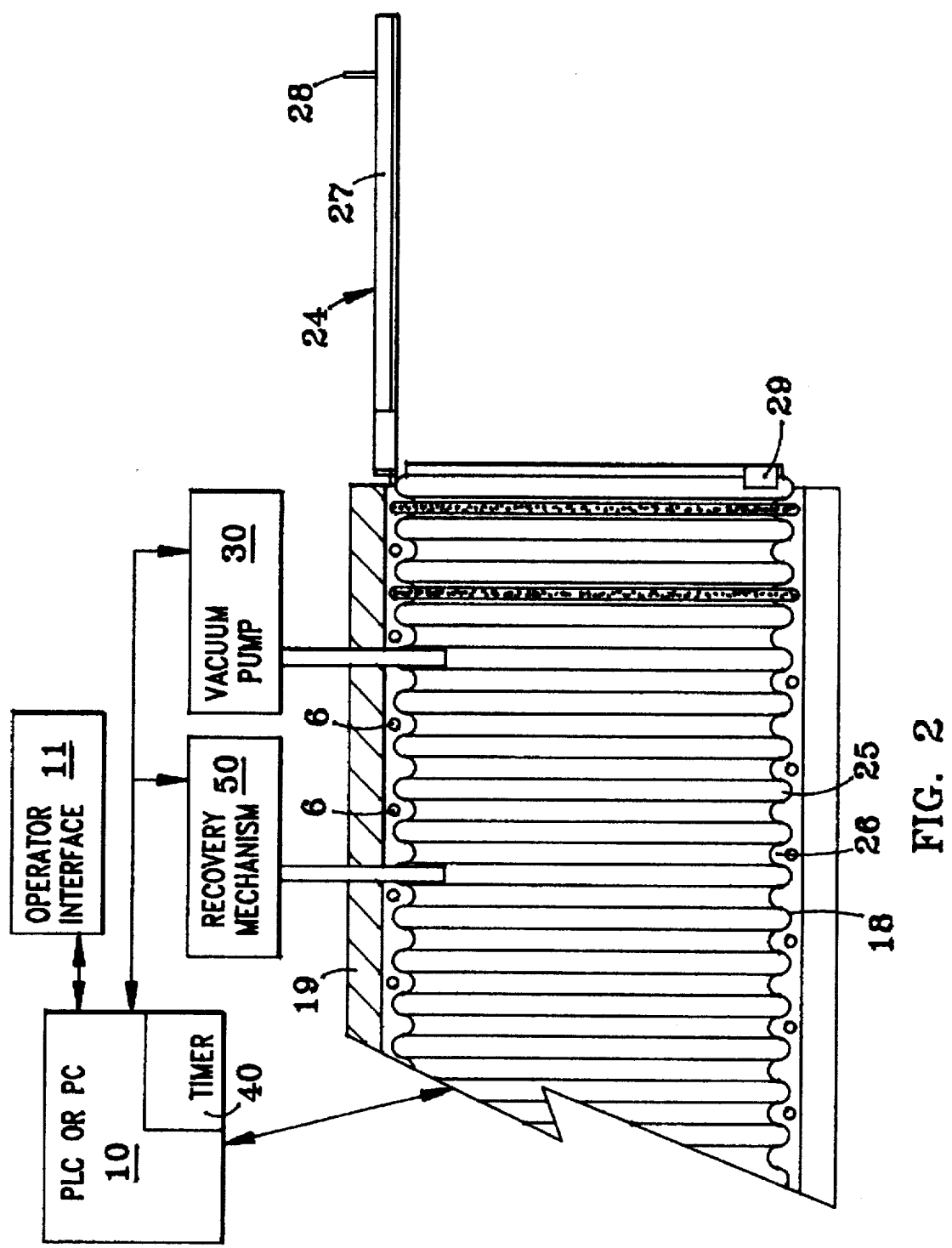
FIG. 2 is a partial top view of the chamber with a door in the open position.

Referring to FIG. 1 and 2, there is depicted a door 24 in the closed and open position respectively. Door 24 includes heating channels 27 and a handle 28. Heating channels 27 allow door 24 to be kept at the chamber temperature and prevents condensation of water vapor on door 24. A double door design allows product 5 to be passed from a non-sterile location through chamber 22 to a sterile location for finished goods. The practice furthers Good Manufacturing Practices (GMP's) at the facility.

Referring back to FIG. 1, a vacuum pump 30 is provided to regulate the pressure within chamber 22. Vacuum pump 30 is controlled by PLC/PC 10 and is sized according to the capacity of chamber 22 of gas sterilizing unit 100. It is common practice to use a liquid ring pump. Any other appropriate type of vacuum pump such as for example a vane type pump could be used and may be dependent upon the application and the necessary duty cycle. Vacuum pump 30 is well known to one with ordinary skill in the art.

Sterilizing unit 100 further includes an exterior cavity 18 and insulating exterior 19. Chamber 22 is located within exterior cavity 18 and insulating exterior 19 surrounds exterior cavity 18. Insulating exterior 19 is preferably made of a flexible poly foam covered with light gauge aluminum. In the fabrication of very large sterilizing units and particularly wall means 20 which defines chamber 22, a space will be provided on the outside of the wall structure through which air may be circulated in order to provide an even temperature distribution throughout chamber 22.

A first circulation fan 17A may be required to circulate the air around the outside of the chamber 22. The circulation may be required if the appropriate heat distribution is not maintained on the wall structure 20. The heat distribution should be +/-2 degrees Fahrenheit.

A second circulation fan 17 is located within chamber 22 of wall structure 20. The purpose of fan 17 is to maintain the gaseous concentrations, heat and humidity homogeneous throughout chamber 22. Fan 17 is typically a three phase motor, ½ HP, 208 voltage, that is manufactured according to the hazardous environment in which it will be used; for example, explosion proof type. The installation of the motor and all the electrical equipment are to be completed according to the latest National Electric Code (NEC), Class I, Division I, Group B. Fan 17 could also be air or hydraulic powered. A unique advantage or feature of the invention is that fan 17 and the motor are inside chamber 22 eliminating the need for high technology rotory seals and the problems which could go with having the motor outside and the fan inside.

Sterilizing unit 100 further includes tubing 6 that is located in alternative grooves 26. The tubing 6 is located in the exterior cavity 18. Tubing 6 is not essential or required for sterilizing unit 100 to effectively operate, but it does aid in the efficiency of sterilizing unit 100. The tubing connections (not shown) are well known to one skilled in the art.

The purpose of tubing 6 is to maintain and provide heat to chamber 22 of wall structure 20 and is typically manufactured of stainless steel with a ¾ inch diameter. A hot liquid (not shown) flows through tubing 6, The liquid is preferably water.

Gas sterilizing unit 100 must include a recovery mechanism 50 for the recovery of the sterilant. Recovery mechanism 50 may be an acid scrubber that converts high concentrations of EO to ethylene glycol. In addition, a catalytic device may be used to convert low concentrations of EO to carbon dioxide and water. Therefore, virtually none of the EO vents to the atmosphere. PLC/PC 10 may also be configured/programmed to automate recovery mechanism 50.

Figure 3:
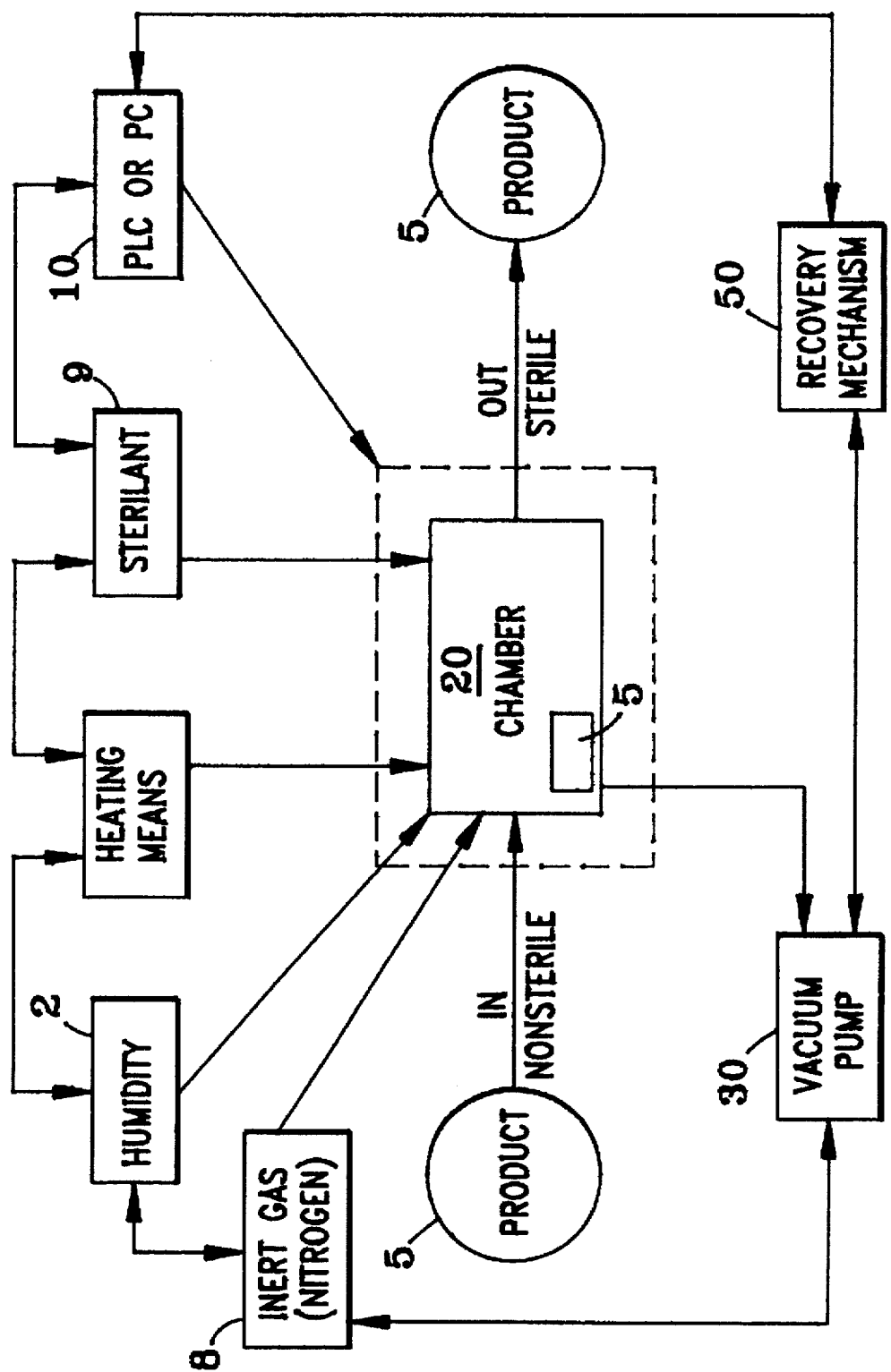
FIG. 3 is a schematic representation of the preferred process of the invention.

Referring to FIG. 3, the process of sterilizing a product 5 is depicted. The process includes the three steps of preconditioning, sterilizing and degassing of product 5. The process may be automated by a PLC/PC 10. Product 5 remains in chamber 22 during the entire process. Each step of the process will be discussed in detail.

The preconditioning step is the first in the process where a non-sterile product is placed in chamber 22 which may be preheated. A vacuum is dram before interjecting steam 2 into product 5, and pressure can be applied by a steam/air mix. The preferred temperature is in a range of 120° F.–130° F. and with a relative humidity in the range of 50%–60%. This process may be repeated several times to dynamically drive heat 3 and steam(humidity) 2 into product 5. The preconditioning process will take approximately 6–10 hours.

The sterilizing process starts by drawing a vacuum. The mount of vacuum depends on the nature of the product in the chamber. The vacuum is followed by a nitrogen injection. A series of vacuum/nitrogen cycles are used (3–5) to ensure that when the EO is injected the percentage of EO mixed with the remaining air will be well below the 3% EO to air ratio. This ensures that the interior of the chamber is below the threshold of the explosive range. The chamber is then filled with a measured mount (typically weight) of EO, (approximately 40 pounds for a 1000 cubic foot chamber). Nitrogen is then added to bring the pressure up to approximately 15 psia. Steam is added for the correct humidity (50–60%), and the cycle goes to a lime hold. When the cycle is complete the vacuum pump is used to transfer the EO to the scrubber.

The preferred process does not require the transporting of product 5 to different locations. The sterilization cycle of the preferred embodiment is completed in less time than present methods, because, product 5 has not lost any heat and humidity 2 during transportation before the sterilization cycle.

Subsequent to the sterilizing cycle a degassing cycle is completed and residual sterilant (EO) is removed from the product. The degassing cycle typically involves a series of vacuums and heated air purges. A vacuum is drawn by vacuum pump 30. The number of vacuums and purges is in the range of from two (2) to about five (5). The degassing cycle may take up to about 24 hours, which is dependent upon the particular product 5. The completion of this cycle results in a sterilized product 5.

It is thought that the present sterilizing unit and many of its attendant advantages is understood from the foregoing description of what are presently considered to be the preferred embodiment of this invention, and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

I claim:

1. A method of gas sterilizing a product comprising the steps of:
   preconditioning said product by interjecting steam and heat to said product;
   loading said product to be sterilized within a sealable chamber said sealable chamber defined by a corrugated wall structure of a sterilizing unit;
   introducing moisture to a predetermined relative humidity within said sealable chamber;
   flushing with an inert gas said sealable chamber;
   heating and cooling of said sealable chamber;
   creating pressure and vacuum within said sealable chamber;
   injecting a controlled amount of said sterilant into said sealable chamber;
   degassing and recovering said gas sterilant from within said sealable chamber;
   controlling, sequence and time of each of said temperature, pressure and vacuum, relative humidity, flushing, injecting said amount of injected sterilant and degassing and recovering of said gas sterilant; and
   whereby a non-sterile product becomes a sterilized product without transferring said product to multiple locations.

2. The method according to claim 1 wherein said step of preconditioning further comprises pressurizing of said product and wherein said heat and said humidity are introduced under dynamic conditions.

3. A gas sterilizing unit that utilizes a sterilant comprising:
   a corrugated wall structure defining a chamber therein;
   at least one door opening into said chamber;
   means for introducing moisture to a predetermined relative humidity within said chamber;
   means for flushing with an inert gas said chamber;
   means for heating and cooling of said chamber;
   means for creating pressure and vacuum within said chamber;
   means for injecting a controlled amount of said sterilant into said chamber;
   means for degassing and recovering said gas sterilant from within said chamber;
   means for controlling, sequence and time of each of said temperature, pressure and vacuum, relative humidity, flushing, injecting said amount of injected sterilant and degassing and recovering of said gas sterilant; and
   wherein a non-sterile product when placed within said chamber and subjected to a gas sterilization process becomes a sterilized product without transferring said product to multiple locations.

4. The gas sterilizing unit according to claim 3 wherein said corrugated wall structure is a corrugated pipe and said gas sterilizing unit further comprises an insulating exterior defining therewithin an exterior cavity where said corrugated wall structure is located within said exterior cavity and said insulating exterior surrounding said exterior cavity.

5. The gas sterilizing unit according to claim 4 further comprising means for circulating a gas, said gas located in said chamber of said sterilizing unit.

6. The gas sterilizing unit according to claim 5 wherein said means for heating and cooling of said chamber further comprises a tubing that is located external and within a plurality of grooves which are integral with said corrugated wall structure, wherein a liquid is circulated through said tubing to maintain a desired temperature in said chamber of said corrugated wall structure.

7. The gas sterilizing unit according to claim 6 further comprising means for recovering and disposing of said sterilant and wherein said means for controlling is a programmable logic controller configured to automate the control of at least one of said temperature, pressure and vacuum, relative humidity, flushing, injecting said amount of injected sterilant and degassing and recovering of said gas sterilant.

8. The gas sterilizing unit according to claim 7 wherein said programmable logic controller is configured to control a plurality of said sterilizing units.

9. The gas sterilizing unit according to claim 7 further comprising means for recovering and disposing of said sterilant and wherein said means for controlling is a programmable computer programmed to automate the control of at least one of said temperature, pressure and vacuum, relative humidity, flushing, injecting said amount of injected sterilant and degassing and recovering of said gas sterilant.

10. The gas sterilizing unit according to claim 6 further comprising means for recovering and disposing of said sterilant and wherein said means for controlling is a programmable computer programmed to automate the control of at least one of said temperature, pressure and vacuum, relative humidity, flushing, injecting said amount of injected sterilant and degassing and recovering of said gas sterilant.

11. The gas sterilizing unit according to claim 9 wherein said programmable computer is programmed to control a plurality of said sterilizing units.

12. The gas sterilizing unit according to claim 3 further comprising means for circulating a gas, said gas located in said chamber of said sterilizing unit.

13. The gas sterilizing unit according to claim 1 wherein said means for heating and cooling of said chamber further comprises a tubing that is located external and within a plurality of grooves which are integral with said corrugated wall structure, wherein a liquid is circulated through said tubing to maintain a desired temperature in said chamber of said corrugated wall structure.

14. The gas sterilizing unit according to claim 13 further comprising means for recovering and disposing of said sterilant and wherein said means for controlling is a programmable logic controller configured to automate the control of at least one of said temperature, pressure and vacuum, relative humidity, flushing, injecting said amount of injected sterilant and degassing and recovering of said gas sterilant.

15. The gas sterilizing unit according to claim 13 further comprising means for recovering and disposing of said sterilant and wherein said means for controlling is a programmable computer programmed to automate the control of at least one of said temperature, pressure and vacuum, relative humidity, flushing, injecting said amount of injected sterilant and degassing and recovering of said gas sterilant.

* * * * *